United States Patent
Tanihata

[11] Patent Number: 5,861,317
[45] Date of Patent: Jan. 19, 1999

[54] AUTOMATIC SAMPLE INJECTOR AND METHOD OF OPERATING SAME

[75] Inventor: Hiroshi Tanihata, Kyoto, Japan

[73] Assignee: Shimadzu Corporation, Kyoto, Japan

[21] Appl. No.: 815,798

[22] Filed: Mar. 12, 1997

[30] Foreign Application Priority Data

Apr. 23, 1996 [JP] Japan .................................... 8-127837

[51] Int. Cl.$^6$ ........................... G01N 1/24; G01N 30/18; G01N 30/24
[52] U.S. Cl. ........................ 436/180; 73/23.41; 73/23.42; 73/863.01; 73/864.87; 95/89; 96/105; 422/89; 422/100; 436/161
[58] Field of Search ............................. 73/23.41, 23.42, 73/61.55, 61.56, 61.59, 863.01, 863.81, 864.13, 864.16, 864.21, 864.81, 864.87; 95/89; 96/105; 422/70, 89, 100; 436/161, 180; 210/198.2, 656; 318/685, 696

[56] References Cited

U.S. PATENT DOCUMENTS

| | | | |
|---|---|---|---|
| 3,855,129 | 12/1974 | Abrahams et al. | |
| 4,336,484 | 6/1982 | Marinko | 318/696 |
| 4,658,194 | 4/1987 | Richter et al. | 318/696 |
| 4,671,123 | 6/1987 | Magnussen, Jr. et al. | 73/864.16 |
| 4,905,526 | 3/1990 | Magnussen, Jr. et al. | 73/864.18 |
| 5,352,963 | 10/1994 | Garand et al. | 318/696 |
| 5,359,271 | 10/1994 | Husher | 318/696 |

*Primary Examiner*—Jan Ludlow
*Attorney, Agent, or Firm*—Majestic, Parsons, Siebert & Hsue P.C.

[57] ABSTRACT

An automatic sample injector for injecting a liquid sample into a vaporization chamber of a gas chromatograph includes a syringe, a plunger adapted to move inside the barrel of this syringe, a stepping motor having a plurality of magnetic poles for moving the plunger up and down inside the barrel, a power source for supplying excitation currents to these magnetic poles, switches for these magnetic poles, and a control unit for controlling the switches or the power source such that the excitation current to one of a pair of the magnetic poles corresponding to a rotary angular position is increased and the excitation current to the other of the pair is simultaneously decreased.

16 Claims, 3 Drawing Sheets

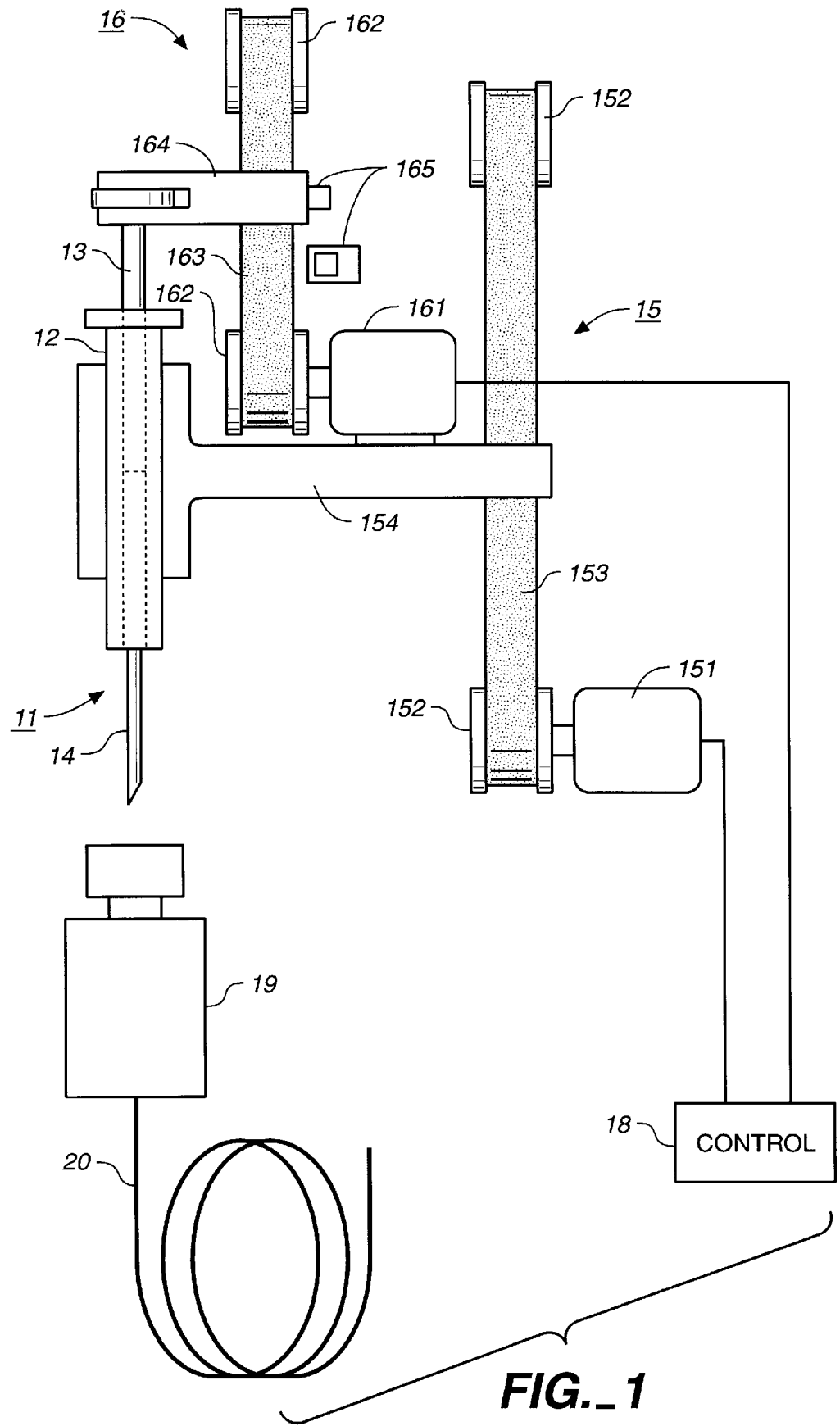
FIG._1

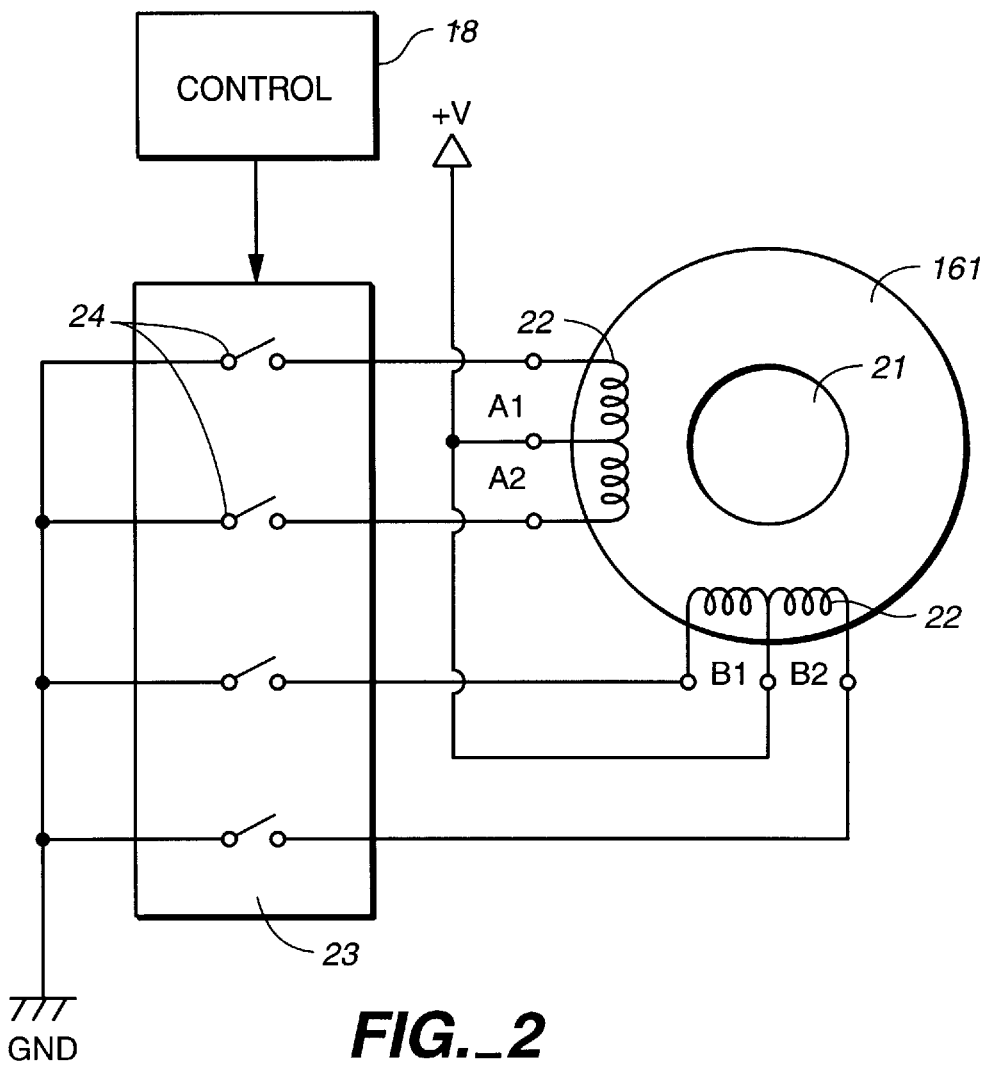
FIG._2
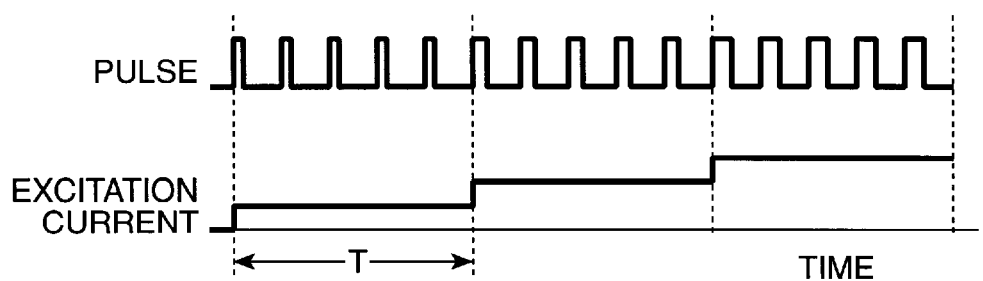
FIG._3

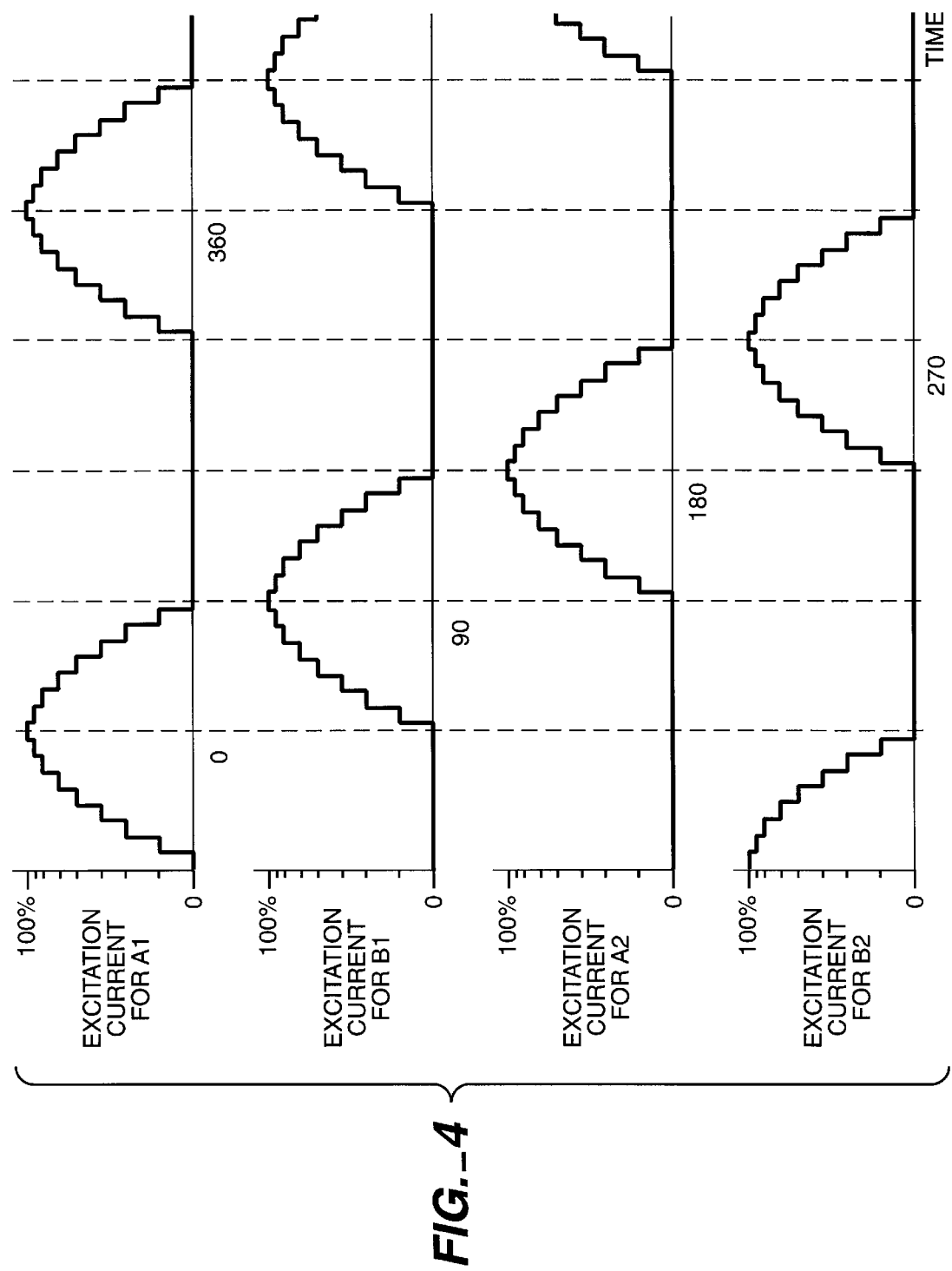
FIG._4

AUTOMATIC SAMPLE INJECTOR AND METHOD OF OPERATING SAME

BACKGROUND OF THE INVENTION

This invention relates to an automatic sample injector for injecting a liquid sample into the vaporization chamber of a gas chromatograph. In particular, this invention relates to an improved method of operating such an automatic sample injector.

A syringe is commonly used for having a liquid sample vaporized for analysis by means of a gas chromatograph. Such a syringe comprises a barrel, a plunger adapted to slide inside the barrel in a liquid-tight relationship therewith, and a needle at the tip of the barrel, having a liquid passage therethrough. After a liquid sample is introduced into the barrel, the needle is caused to penetrate a septum (a rubber membrane) and is inserted into the vaporization chamber such that the liquid sample can be dispersed. The liquid sample which has been atomized is vaporized by heat and is transported into the column by a carrier gas introduced into the vaporization chamber.

An automatic sample injector is for carrying out these processes automatically and comprises a syringe-driving mechanism for moving the syringe with respect to the vaporization chamber and inserting the needle into the vaporization chamber and a plunger-driving mechanism for moving the plunger with respect to the barrel for sucking in a liquid sample into the barrel or injecting it out of the barrel.

Roughly speaking, the plunger-driving mechanisms can be divided into two kinds, one being by an open loop control by means of a stepping motor and the other being by a closed loop servo control by means of a DC motor. According to the former, the opening and closing of the switches for each magnetic pole of the stepping motor are controlled such that the rotor can be rotated by angles determined by the distribution of the magnetic poles. The advantage of this method is that the circuit is of a simple structure and is easy to control because it is an open loop control. For this reason, many prior art automatic sample injectors made use of this kind of mechanism.

With prior art driving mechanisms, however, rotary motion of the rotor of the stepping motor was accompanied by pulsation (or so-called "cogging"), and it was difficult to move the plunger smoothly at a constant speed. As a result, gas foams were likely to be generated when a sample is sucked in, adversely affecting the accuracy in the amount of the sample to be sucked in.

SUMMARY OF THE INVENTION

It is therefore an object of this invention to provide an improved automatic sample injector of a simple structure capable of limiting the generation of foams at the time of sample introduction by operating the plunger smoothly by means of a stepping motor.

An automatic sample injector embodying this invention, with which the above and other objects can be accomplished, may be characterized as comprising not only a syringe and a plunger adapted to move inside the barrel of this syringe, but also a stepping motor having a plurality of magnetic poles for moving the plunger up and down inside the barrel, a power source for supplying excitation currents to these magnetic poles, switches for these magnetic poles, and a control unit for controlling the switches or the power source such that the excitation current to one of a pair of the magnetic poles corresponding to a rotary angular position is increased and that to the other of the pair is simultaneously decreased.

With an automatic sample injector embodying this invention, the control unit operates the stepping motor in a so-called micro-step driving mode when the plunger is pulled out in order to suck in the liquid sample into the barrel of the syringe. The angular positions of the rotor of the stepping motor (0–360 degrees) are determined by the magnetic flux of the magnetic field generated by a pair of magnetic poles corresponding to the angular position. Since the magnetic flux depends on the intensity of the excitation current for the pair of magnetic poles, the rotor of the stepping motor rotates by small angles within the range of the specified angular position determined by the pair of magnetic poles if the excitation current for one of the magnetic poles is gradually increased and that of the other pole is gradually decreased.

As an example, if a constant-current power source is used, the control unit will increase the duty ratio of high-frequency pulse signals for opening and closing one of the switches for the pair of magnetic poles, decreasing that of the other. As a result, the average excitation current through one of the magnetic poles per unit time increases while that of the other magnetic pole decreases, causing the rotor of the stepping motor to rotate by small angles.

In order to pull the plunger at a constant speed as much as possible, it is desirable that the torque be constant, without changing according to its angular position. For this reason, the control unit preferably distributes the currents to the pair of magnetic poles such that the vector-sum of the individual torques generated by the magnetic fields of these two magnetic poles will approximately be a constant.

According to this invention, the plunger can be moved at smaller steps than in units corresponding to the rotary angles determined by the positions of the magnetic poles of the stepping motor. This makes it possible to move the plunger more smoothly and, since the generation of foams can be reduced, samples can be sucked in with improved accuracy.

Since the plunger can be positioned with more accuracy than before, furthermore, the amount of the sample to be sucked in can be determined in smaller units. This makes more accurate chromatographic analyses possible.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a schematic drawing for showing the structure of an automatic sample injector embodying this invention;

FIG. 2 is a schematic structural diagram of the motor-driving part of the automatic sample injector of FIG. 1;

FIG. 3 is a waveform diagram for showing the control of the motor-driving part of FIG. 2; and FIG. 4 is a waveform diagram for showing the control of the motor-driving part when a sample is being sucked in.

DETAILED DESCRIPTION OF THE INVENTION

As shown in FIG. 1, an automatic sample injector 10 embodying this invention may be characterized as comprising a syringe-driving mechanism 15 for moving a syringe 11 (having a barrel 12 and a plunger 13) vertically up and down and a plunger-driving mechanism 16 for moving the plunger 13 of the syringe 11 vertically up and down. The syringe-driving mechanism 15 includes a syringe-driving motor 151 and a pair of pulleys 152, of which the positions are fixed with respect to the vaporization chamber 19 of a gas chromatograph, as well as a belt 153 stretched between these pulleys 152 and a syringe clamper 154 with one end attached to the belt 153.

The plunger-driving mechanism 16 includes a plunger-driving motor 161 affixed to the syringe clamper 154, a pair of pulleys 162, a belt 163 stretched between these pulleys 162, and a plunger clamper 164 with one end attached to this belt 163. The plunger-driving mechanism 16 is further provided with a home-position sensor 165 including light emitting and receiving elements affixed to a side of the syringe clamper 154 and a reflecting mirror affixed to the plunger clamper 164. When the plunger 13 is at the most deeply pushed-in position inside the barrel 12 of the syringe 11 ("home position"), the reflecting mirror returns the light from the light emitting element to the light receiving element, and the home-position sensor 165 thereby detects that the plunger 13 is at its home position.

The plunger-driving motor 161 is a stepping motor. As shown schematically in FIG. 2, there are four magnetic poles 22 (A1, A2, B1 and B2, A2 and B2 being of opposite polarity to A1 and B1) formed on the side of the stator of the stepping motor 161, and there are switches 24 for passing or not passing a current through each of the magnetic poles 22. Each switch 24 may be a FET switch, together forming a FET array controlled by a control unit 18 which serves to close the individual switches 24 of the FET array 23 for a specified length of time so as to excite the corresponding ones of the magnetic poles 22 to thereby cause the rotor 21 of the stepping motor 161 to rotate by a specified angle.

With the stepping motor 161 thus formed as shown in FIG. 2, if the magnetic poles 22 are excited by one phase in the order of A1, B1, A2 and B2, the rotor 21 will rotate by step angles (one step angle being about 1.8° for a general 2-phase stepping motor). In order to rotate the rotor 21 by one step angle by one-phase excitation, the control unit 18 sends a pulse to the switches 24 comprising many small (high-frequency) pulse signals and its duty ratio is controlled by the control unit 18.

If pulse signals with a small duty ratio are inputted to the switches 24 as shown in FIG. 3, the average excitation current to the corresponding magnetic pole 22 during a specified period of time T1 is small and the torque is correspondingly weak. If pulse signals with a large duty ratio are inputted to the switches 24, on the other hand, the average excitation current is large and the torque is correspondingly strong.

When a gas chromatographic analysis is actually carried out, the control unit 18 will first raise the syringe 11 to its highest position by means of the syringe-driving mechanism 15, allowing a container, or a vial (not shown), containing a sample to be placed in the space between the needle 14 of the syringe 11 and the vaporization chamber 19. The syringe-driving mechanism 15 is activated again to lower the syringe 11 so as to insert the needle 14 into the sample inside the vial, the plunger-driving mechanism 16 is activated to pull up the plunger 13 so as to suck in a desired amount of the sample into the interior of the barrel 12 of the syringe 11.

While the sample is thus being sucked in, the control unit 18 changes the duty ratios of the pulse signals inputted to switches 24 for two of the magnetic poles 22 corresponding to each step angle of the stepping motor 161 such that the average excitation currents through these magnetic poles 22 change in step-wise fashions. This is illustrated in FIG. 4 wherein each step angle is divided into eight parts and duty ratio is changed for each such that the excitation current through each magnetic pole 22 changes in eight steps between 0–100% (the maximum average excitation current to be supplied to the magnetic pole 22 being 100%). Between rotary angular positions of 0 and 1 step angle, for example, the average currents passed through magnetic poles A1 and B1 are as shown in FIG. 4, and the rotor 21 rotates by ⅛ of one step angle according to these average excitation currents.

In summary, the rotor 21 of the stepping motor 161 rotates in smaller angular steps than by prior art one-phase or 1-2-phase excitation whereby the rotor rotates in units of one step angle or one-half step angle. Thus, the pulsation of the torque is much smaller than was before. As a result, the plunger 13 can be pulled up smoothly at a nearly constant speed, and there are hardly any foams formed in the sample sucked into the interior of the barrel 12 of the syringe 11.

Since the amount of the sample which is sucked in is determined by the rotary angle of the rotor 21, the control unit 18 transmits to the FET array 23 a number of pulse signals corresponding to the desired amount of sample to be sucked in. Since the rotary angle of the rotor 21 can be controlled according to this invention in smaller units (about ⅛ of the step angle), the amount of sample to be sucked in can also be controlled with correspondingly smaller steps with increased accuracy.

After the sample has been sucked in, the plunger 13 is raised to take the needle 14 of the syringe 11 out of the vial, and the vial is removed. Next the syringe-driving mechanism 15 is activated to lower the syringe 11, thereby causing the needle 14 to be inserted into the vaporization chamber 19 by penetrating the septum at the top of the vaporization chamber 19. The lowering of the syringe 11 is stopped when the tip of the needle 14 reaches a specified position inside the vaporization chamber 19. Immediately thereafter, the plunger-driving mechanism 16 pushes down the plunger 13 until its lower end reaches the bottom of the barrel 12, thereby ejecting the desired amount of the sample into the vaporization chamber 19. For this operation, the control unit 18 does not carry out the microstep driving described above, but causes the sample to be ejected quickly by the ordinary two-phase excitation. The sample injected into the vaporization chamber 19 is vaporized by heat and transported to the column 20 by a carrier gas.

The disclosure described above is not intended to limit the scope of the invention. Many modifications and variations are possible within the scope of the invention. For example, the average excitation currents need not be varied by changing the duty ratios of the pulse signals for opening and closing the switches 24. This may be accomplished by using a power source with variable voltage for supplying power to each magnetic pole and causing the control unit 18 to vary their output voltages. The number of segments into which each step angle is divided for finer control may be increased from eight, say, to sixteen.

What is claimed is:

1. An automatic sample injector for injecting a liquid sample into a vaporization chamber of a gas chromatograph, said automatic sample injector comprising:

a syringe having a barrel and a plunger adapted to move inside said barrel;

a stepping motor having a rotor and more than two pairs of magnetic poles for rotating said rotor by step angles and thereby causing said plunger to move inside said barrel, each of said pairs of magnetic poles corresponding to one of said step angles and to a rotary angular position of said rotor;

a power source for supplying excitation currents to said magnetic poles;

switches individually associated with said magnetic poles to pass or not pass said excitation currents to individual ones of said magnetic poles; and control means for controlling said excitation currents to each of said pairs of magnetic poles within a corresponding one of said step angles such that the vector-sum of torques generated by magnetic fields of said each pair of magnetic poles is approximately constant within said corresponding step angle by increasing average excitation current to one of said each pair and simultaneously decreasing average excitation current to the other of said each pair within said corresponding step angle.

2. The automatic sample injector of claim 1 wherein said control means controls said power source to thereby increase and decrease said excitation currents to said pairs of magnetic poles.

3. The automatic sample injector of claim 1 wherein said control means controls said switches to thereby increase and decrease said excitation currents to said pairs of magnetic poles.

4. The automatic sample injector of claim 1 wherein said control means changes said excitation currents to said pairs of magnetic poles in a plural number of steps for each of said step angles of said stepping motor.

5. The automatic sample injector of claim 2 wherein said control means changes said excitation currents to said pairs of magnetic poles in a plural number of steps for each of said step angles of said stepping motor.

6. The automatic sample injector of claim 3 wherein said control means changes said excitation currents to said pairs of magnetic poles in a plural number of steps for each of said step angles of said stepping motor.

7. The automatic sample injector of claim 1 wherein said step angles are about 1.8°.

8. The automatic sample injector of claim 1 wherein said control means increase and decrease excitation currents through each pair of said magnetic poles in eight steps over each of said step angles.

9. A method of controlling an automatic sample injector for injecting a liquid sample into a vaporization chamber of a gas chromatograph, said automatic sample injector having a syringe with a barrel and a plunger adapted to move inside said barrel; said method comprising the steps of:

providing a stepping motor having a rotor and more than two pairs of magnetic poles for rotating said rotor by step angles and thereby causing said plunger to move inside said barrel, each of said pairs of magnetic poles corresponding to one of said step angles and to a rotary angular position of said rotor; and controlling said excitation currents to each of said pairs of magnetic poles within a corresponding one of said step angles such that the vector-sum of torques generated by magnetic fields of said each pair of magnetic poles is approximately constant within said corresponding step angle by increasing average excitation current to one of said each pair and simultaneously decreasing average excitation current to the other of said each pair within said corresponding step angle.

10. The method of claim 9 wherein said excitation currents are increased and decreased simultaneously by controlling a power source for said excitation currents.

11. The method of claim 9 wherein said excitation currents are increased and decreased simultaneously by controlling switches which are individually associated with said magnetic poles to pass or not pass excitation currents to individual ones of said magnetic poles.

12. The method of claim 9 wherein said excitation currents are increased and decreased in a plural number of steps for each of said step angles of said stepping motor.

13. The method of claim 10 wherein said excitation currents are increased and decreased in a plural number of steps for each of said step angles of said stepping motor.

14. The method of claim 11 wherein said excitation currents are increased and decreased in a plural number of steps for each of said step angles of said stepping motor.

15. The method of claim 9 wherein said step angles are about 1.8°.

16. The method of claim 9 wherein each of said excitation is increased or decreased in eight steps over each of said step angles.

* * * * *